(12) United States Patent
Wang et al.

(10) Patent No.: US 7,682,553 B2
(45) Date of Patent: Mar. 23, 2010

(54) BALLOON STRUCTURE WITH PTFE COMPONENT

(75) Inventors: Lixiao Wang, Long Lake, MN (US); John Jianhua Chen, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1533 days.

(21) Appl. No.: 10/797,996

(22) Filed: Mar. 11, 2004

(65) Prior Publication Data

US 2004/0170782 A1 Sep. 2, 2004

Related U.S. Application Data

(62) Division of application No. 09/514,929, filed on Feb. 28, 2000, now Pat. No. 6,756,094.

(51) Int. Cl.
*B29C 49/22* (2006.01)
*A61M 25/10* (2006.01)

(52) U.S. Cl. .................. 264/545; 264/573; 264/516; 604/96.01; 606/194

(58) Field of Classification Search ............... 264/535, 264/545, 573, 512, 515, 516; 604/96.01; 606/194

See application file for complete search history.

(56) References Cited

U.S. PATENT DOCUMENTS

| | | | | |
|---|---|---|---|---|
| 3,376,238 A * | 4/1968 | Gregorian et al. | ............ | 264/49 |
| 3,953,566 A | 4/1976 | Gore | ............ | 264/288 |
| 4,187,390 A | 2/1980 | Gore | ............ | 174/102 |
| 4,332,035 A | 6/1982 | Mano | ............ | 3/1.4 |
| 4,490,421 A | 12/1984 | Levy | ............ | 428/35 |
| 4,503,569 A | 3/1985 | Dotter | ............ | 3/1.4 |
| 4,733,665 A | 3/1988 | Palmaz | ............ | 128/343 |
| 4,830,003 A | 5/1989 | Wolff et al. | ............ | 128/343 |
| 4,990,155 A | 2/1991 | Wilkoff | ............ | 606/191 |
| 5,163,989 A | 11/1992 | Campbell et al. | ............ | 65/110 |
| 5,269,755 A | 12/1993 | Bodicky | ............ | 604/53 |
| 5,304,340 A | 4/1994 | Downey | ............ | 264/521 |
| 5,338,299 A | 8/1994 | Barlow | ............ | 604/96 |
| 5,348,538 A | 9/1994 | Wang et al. | ............ | 604/96 |
| 5,358,487 A | 10/1994 | Miller | ............ | 604/96 |
| 5,447,497 A | 9/1995 | Sogard et al. | ............ | 604/101 |
| 5,480,711 A | 1/1996 | Ruefer | ............ | 428/315.5 |
| 5,499,973 A | 3/1996 | Saab | ............ | 604/96 |
| 5,587,125 A | 12/1996 | Roychowdhury | ............ | 264/515 |
| 5,620,649 A | 4/1997 | Trotta | ............ | 264/515 |
| 5,752,934 A | 5/1998 | Campbell et al. | ............ | 604/96 |
| 5,772,669 A | 6/1998 | Vrba | ............ | 606/108 |
| 5,797,877 A | 8/1998 | Hamilton et al. | ............ | 604/96 |
| 5,807,520 A | 9/1998 | Wang et al. | ............ | 264/520 |
| 5,820,594 A | 10/1998 | Fontirroche et al. | ............ | 604/96 |
| 5,833,657 A | 11/1998 | Reinhardt et al. | ............ | 604/96 |
| 5,843,116 A * | 12/1998 | Crocker et al. | ............ | 606/192 |
| 5,868,704 A | 2/1999 | Campbell et al. | ............ | 604/96 |
| 5,879,369 A | 3/1999 | Ishida | ............ | 606/194 |
| 5,908,406 A | 6/1999 | Ostapchenko et al. | ......... | 604/96 |

(Continued)

*Primary Examiner*—Matthew J. Daniels
(74) *Attorney, Agent, or Firm*—Vidas, Arrett & Steinkraus, P.A.

(57) ABSTRACT

A medical balloon having a high burst strength and the ability to return to its preinflation diameter following repeated inflation may be prepared from a first inner layer of material, a second intermediate layer of expanded PTFE and a third outer layer of material.

5 Claims, 5 Drawing Sheets

U.S. PATENT DOCUMENTS

| | | | |
|---|---|---|---|
| 6,027,477 A | 2/2000 | Kastenhofer | 604/96 |
| 6,136,258 A | 10/2000 | Wang et al. | 264/514 |
| 6,328,925 B1 | 12/2001 | Wang et al. | 264/512 |
| 6,482,348 B1 | 11/2002 | Wang et al. | 264/514 |
| 6,572,813 B1 | 6/2003 | Zhang et al. | 264/519 |

* cited by examiner

BALLOON STRUCTURE WITH PTFE COMPONENT

CROSS REFERENCE TO RELATED APPLICATIONS

This application is a divisional of U.S. application Ser. No. 09/514,929, filed on Feb. 28, 2000 the contents of which is hereby incorporated by reference

FIELD OF THE INVENTION

The present invention relates generally to medical balloons made at least in part from polytetrafluoroethylene.

BACKGROUND OF THE INVENTION

The use of medical balloons for dilatation of a body vessel as well as for expansion and seating of a medical devices such as a stent is well known. Medical balloon may be made of a single layer of material or of multiple layers of material. In the case of multilayer balloons, the multiple layers may be of the same or different materials.

A variety of materials have been used for making medical balloons including thermoplastic polyurethanes (TPU), polyethylene, polyesters such as polyethylene terephthalate (PET) including non-compliant PET, Arnitel, Hytrel, polyetherether ketone (PEEK), block copolymers of polyether polymers and polyamides (polyether block amides) such as Pebax® (all grades) available from Elf Atochem North America, block copolymers of polyether and polyester polymers such as Hytrel® available from E.I. DuPont de Nemours & Co. in Wilmington, Del., Teflon®, polyamides such as nylon-11 and nylon-12, block polyimides, polytetrafluoroethylene (PTFE), polyolefins such as polyethylenes (PE) and polypropylenes (PP), synthetic rubbers including SBR and EPDM, as well as other polyolefins and silicone elastomers. For catheter balloons used in coronary angioplasty preferred polymeric substrates are PET, nylon and PE. The specific choice of materials depends on the desired characteristics of the balloon.

Of these materials, PTFE is of interest for use in medical balloons because of its low coefficient of friction, chemical resistance, flexibility and strength. Because of the physical properties of PTFE, however, the material cannot be processed in the same way that conventional thermoplastic elastomers are processed.

The use of polytetrafluoroethylene (PTFE) and expanded PTFE (EPTFE) in implantable medical devices such as balloons has been disclosed in U.S. Pat. Nos. 5,752,934 and 5,868,704 both of which disclose a balloon comprised of a porous EPTFE layer and an elastomeric or inelastic layer. The EPTFE films may serve either as a coat for a balloon or as an integral part of a balloon in the form of an outer layer. The balloons disclosed therein are formed from a helically wound porous EPTFE film. In one example, twenty layers of EPTFE film are used to form the EPTFE portion of the balloon. As a result, these balloons tend to have a large profile.

It is desirable to produce a medical balloon which has some of the properties of a PTFE balloon and yet has a low profile. More specifically, it is a goal of the present invention to provide a non-compliant EPTFE balloon which has a high burst strength and the ability to return to its preinflation diameter following repeated inflation/deflation cycles. To that end, the present invention provides medical balloons having one or more EPTFE layers disposed between an inner balloon material and an outer balloon material.

All US patents and all other published documents mentioned anywhere in this application are incorporated herein by reference in their entirety.

BRIEF SUMMARY OF THE INVENTION

The present invention is directed to medical balloons comprising EPTFE and similar materials as well as to catheters with such balloons mounted thereon. At least a portion of the medical balloon disclosed herein includes an inner layer, an intermediate layer and an outer layer. The intermediate layer disposed between the inner and outer layers is formed of EPTFE. A wide variety of materials may be used for the inner and outer layers including thermoplastic materials, elastomeric materials and thermoplastic elastomeric materials.

The intermediate expanded PTFE layer may extend over the entire length of the balloon or may extend over only a portion of the balloon.

The present invention is also directed to a balloon having a first body portion with a generally linear compliance curve to burst pressure and a second body portion having a stepped compliance curve.

The balloons of the present invention may be formed in a variety of ways including coating the interior and exterior of an EPTFE tube with first and second materials or laminating an inner and an outer layer of material to one or more layers of EPTFE at a suitable temperature. Alternatively, the balloon may be formed by inserting a PTFE or an EPTFE tube between inner and outer tubes of other materials and suitably shaping the tubes at a desired temperature via the application of tension and/or radially outward pressure such as by blowing. Where a PTFE tube is used, the PTFE may be expanded during the step of radially expanding the tube so as to form an EPTFE tube. The EPTFE tube may also be formed by expanding an extruded tube of PTFE separate from radial expansion or may be formed of a sheet of EPTFE that is disposed in a tubular form.

The present invention is also directed to methods of preparing the inventive balloon. One such method involves coating a tube of PTFE or EPTFE on the inside and outside. Another method involves concentrically disposing inner, outer and intermediate tubes and joining the tubes together via lamination or heating or any other suitable technique. Yet another method involves co-extruding the three or more layers of balloon material.

The inventive catheters include the medical balloon disclosed herein disposed about a tube and having an inflation lumen in fluid communication with the balloon. The inventive catheter may be dilatation catheters, a medical device delivery catheter or any other catheter that carries a medical balloon.

BRIEF DESCRIPTION OF THE SEVERAL VIEWS OF THE DRAWING(S)

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

The inventive medical balloons disclosed herein may be used for a variety of purposes including angioplasty and embolectomy as well as for the expansion of medical devices such as stents, grafts, stent-grafts and vena-cava filters.

The inventive medical balloons are generally characterized by the presence of at least one intermediate layer of a fluorinated polymeric material such as PTFE, or EPTFE or materials such as a linear high density polyethylene disposed between an inner layer of a first balloon material different from the material of the intermediate layer and an outer layer of a second balloon material different from the material of the intermediate layer. The first and second balloon materials may be the same or different from each other.

Figure 1A:
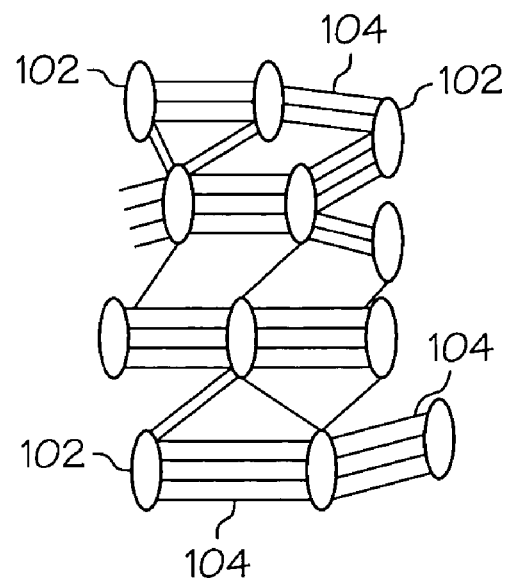
FIG. 1a shows a node and fibril structure for EPTFE have substantially parallel fibrils.
Figure 1B:
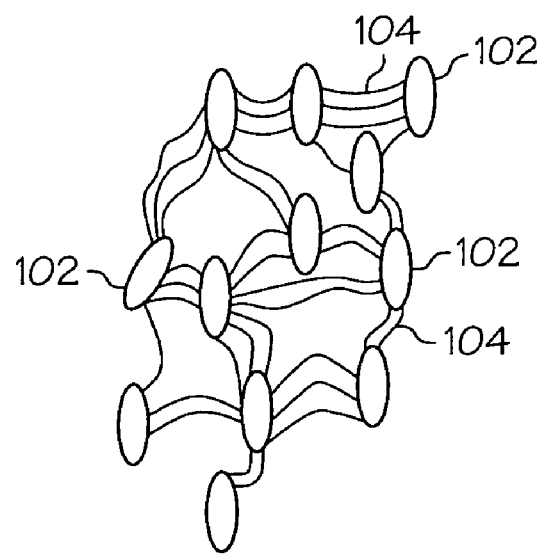
FIG. 1b shows a node and fibril structure for EPTFE in which the fibrils are bent.

A suitable form of PTFE may be made in accordance with U.S. Pat. No. 5,480,711. An example of a PTFE material is manufactured by DuPont de Nemours & Co. in Wilmington, Del. under the tradename of Teflon®. Suitable EPTFE films may be made in accordance with U.S. Pat. Nos. 3,953,566 and 4,187,390. This form of EPTFE, shown in FIG. 1a, has a microstructure consisting of nodes 102 interconnected by fibrils 104 which are all substantially parallel to the direction of expansion. More desirably, the EPTFE used in the inventive balloons disclosed herein will have a microstructure as shown in FIG. 1b consisting of nodes 102 interconnected by bent or wavy fibrils 104. This latter form of EPTFE, disclosed in U.S. Pat. No. 5,752,934, is more elastic than the EPTFE disclosed in either U.S. Pat. No. 3,953,566 or U.S. Pat. No. 4,187,390 and is characterized by a rapid recovery of greater than 5.5%. All patents referred to are herein incorporated in their entirety.

Figure 2:
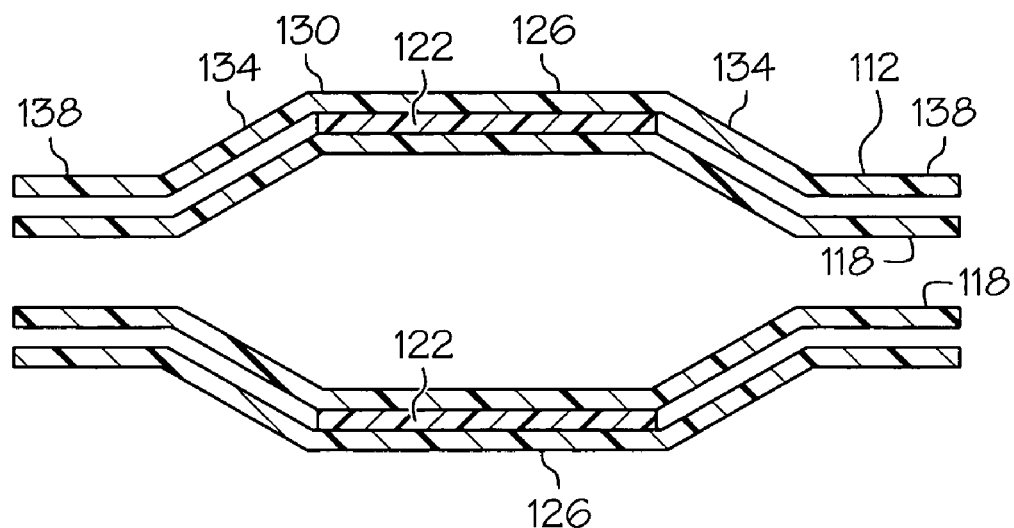
FIG. 2 shows a longitudinal cross section view of a medical balloon with an intermediate layer extending only over the body portion of the balloon.

In one embodiment, as shown in FIG. 2, inventive balloon 112 is formed of three layers including an inner layer 118, an intermediate layer 122 formed of expanded PTFE and an outer layer 126. In the embodiment shown in FIG. 1, intermediate layer 122 extends over body portion 130 of balloon 110.

Figure 3:
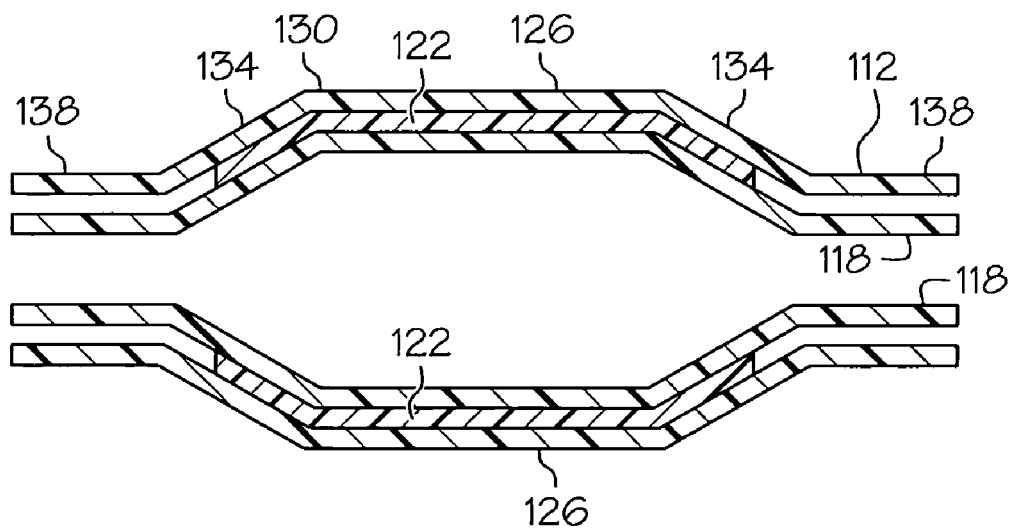
FIG. 3 shows a longitudinal cross section view of a medical balloon with an intermediate layer extending over the cone portion of the balloon.

In another embodiment, shown in FIG. 3, intermediate layer 122 extends beyond the body portion to at least a portion of the proximal and distal cone 134 portions.

Figure 4:
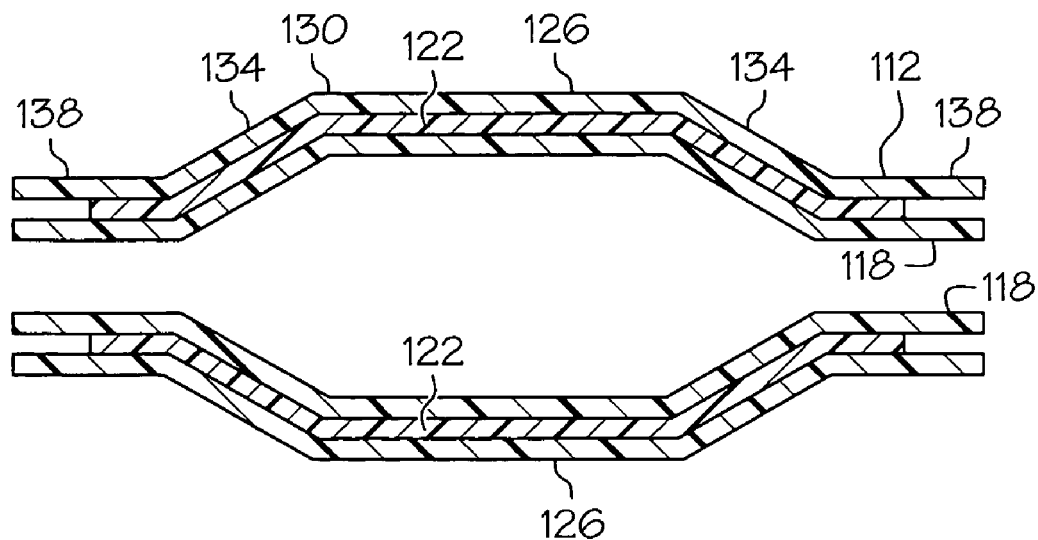
FIG. 4 shows a longitudinal cross section view of a medical balloon with an intermediate layer extending over a part of the waist portion of the balloon.

In another embodiment, shown in FIG. 4, intermediate layer 122 extends over at least a portion of proximal and distal waist 138 portions.

Figure 5:
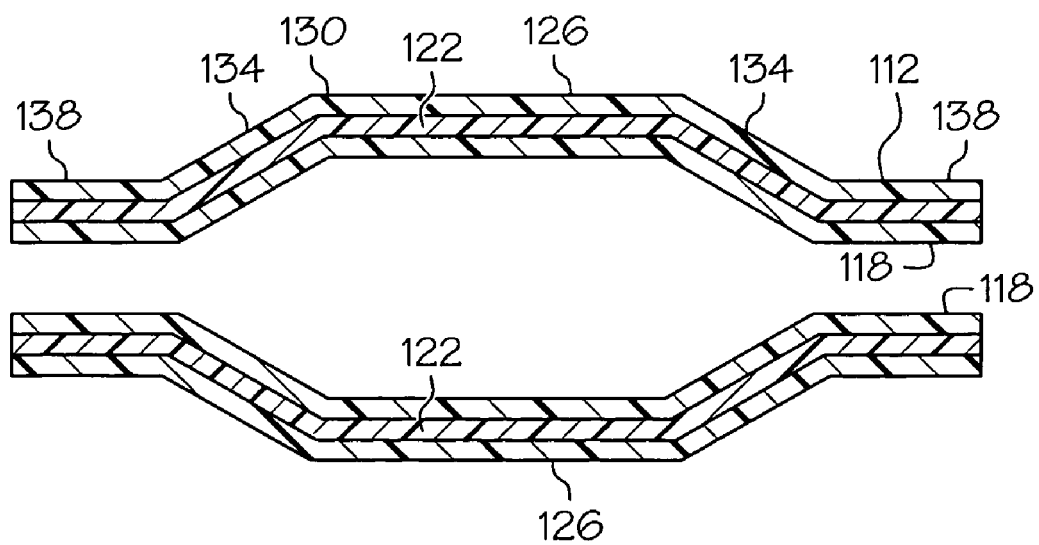
FIG. 5 shows a longitudinal cross section view of a medical balloon with an intermediate layer extending over the waist portion of the balloon.

In another embodiment, shown in FIG. 5, intermediate layer 122 is coextensive with inner layer 118 and outer layer 126 over the length of balloon 110.

Figure 6:
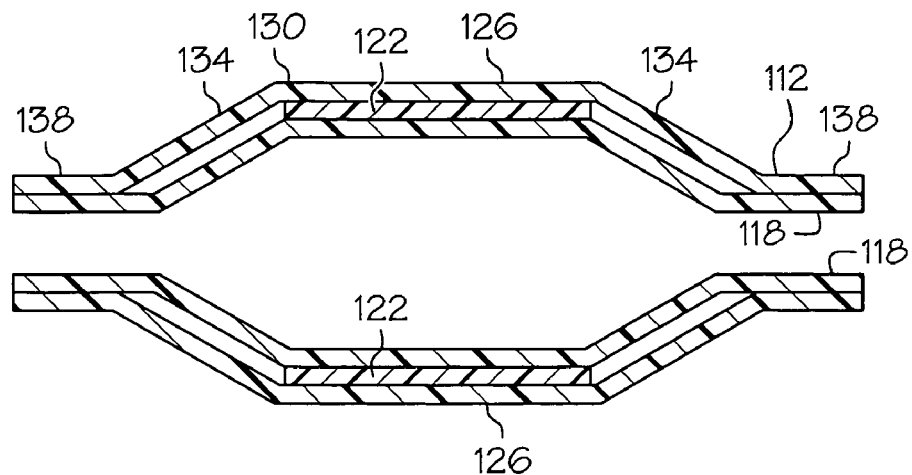
FIG. 6 shows a longitudinal cross section view of a medical balloon with an encapsulated intermediate layer.

The invention is also directed to a medical balloon, shown at 112 in FIG. 6, containing at least an inner layer 118, an outer layer 126 and an intermediate layer 122. Intermediate layer 122 is enclosed or encapsulated by inner layer 118 and outer layer 126. Inner layer 118 and outer layer 126 are joined together so as to encapsulate intermediate layer 122. As shown in FIG. 6, inner layer 118 and outer layer 126 are joined at proximal and distal waists 138. They may also be joined in cone portions 134.

In yet another embodiment, the invention is directed to a medical balloon containing, as above, an innermost layer, an outer most layer disposed exterior to the innermost layer, and an intermediate layer, disposed between the innermost layer and the outermost layer. The intermediate layer is constructed of a material having a node structure connected by multiple fibers. Suitable materials having such a structure include expanded PTFE and high density polyethylene. Desirably, the fibers will be bent or wavy.

In yet another embodiment, the invention is directed to a medical balloon having, as above, an innermost layer, an outer most layer disposed exterior to the innermost layer, and an intermediate layer, disposed between the innermost layer and the outermost layer. The intermediate layer is constructed of a material which, when expanded, has a node structure connected by multiple fibers.

The above-described inventive balloons may be prepared, via the choice of suitable inner and outer materials, so as to display normal distention at low inflation pressures and reduced distention at high pressures.

Figure 7A:
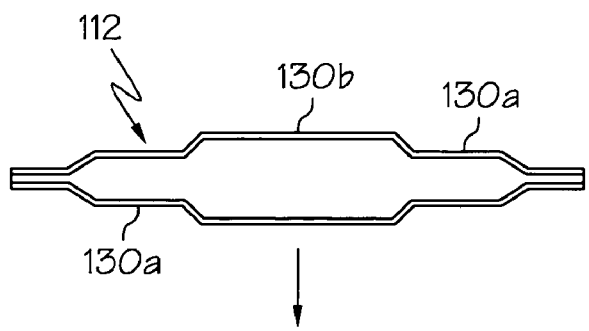
FIG. 7a shows a schematic view of a fully inflated balloon.

In another embodiment, the invention is directed to a balloon, shown at 112 in FIG. 7a, having first and second adjacent body longitudinal portions, labeled 130a and 130b respectively. First body portion 130a has a generally linear compliance curve to burst pressure. Second body portion 130b has a stepped compliance curve characterized by a low pressure segment generally collinear with the corresponding segment of the first body portion, a transition segment during which the balloon expands rapidly relative to the first body portion and a high pressure segment during which the compliance curve of the second portion expands slowly relative to the transition region. Balloon 112 is shown in the partially inflated state in FIG. 7b at a pressure where the compliance curves of the first and second body portions are generally collinear. A cross-sectional view of balloon 112 is shown in FIG. 7c. Inner layer 118 and outer layer 126 extend over the length of the balloon. An intermediate layer 122 extends along the length of body portion 130a on both sides of the balloon and is discontinuous in the region of second body portion 130b. The discontinuity is shown at 132.

Figure 7B:
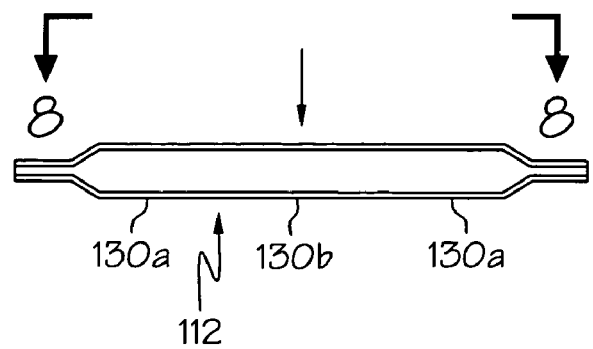
FIG. 7b shows a schematic view of a partially inflated balloon.
Figure 7C:
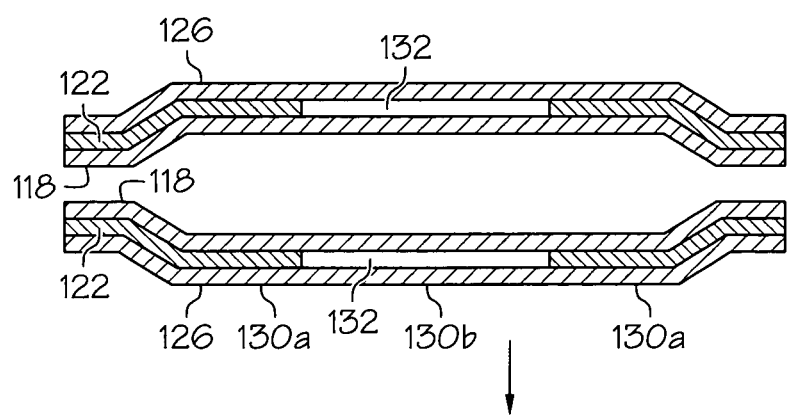
FIG. 7c shows a longitudinal cross section of the balloon of FIG. 7b along lines 8-8.

In the embodiment of FIGS. 7a-c, the inner and outer materials are characterized by a compliance curve similar to that of the second portion of the balloon while the intermediate layer is characterized by a compliance curve similar to that of the first portion of the balloon.

Desirably, the intermediate layer will be formed of a fluoropolymer such as PTFE or the expanded PTFE's discussed above, or of a high density polyethylene.

Balloons whose sections are characterized by different compliance curves are discussed more generally in U.S. Pat. Nos. 574,985, 5,447,497 and 5,358,487 incorporated by reference herein in their entirety.

The instant invention is also directed to methods of forming an inventive balloon preform as well as a balloon. In one such method, a tube made of EPTFE is provided. The EPTFE tube may be formed of an extruded PTFE tube which has been stretched under suitable conditions or stretched and compressed under suitable conditions. A suitable extruded EPTFE tube may be made in accordance with U.S. Pat. No. 5,505,887 incorporated by reference herein in its entirety. The EPTFE tube may also be formed by disposing a sheet of EPTFE (desirably with substantially parallel or bent fibrils) in a tubular form and sealing the two adjacent edges by heating the tube at a suitable temperature. This sheet may be formed of one layer of EPTFE, or of a multitude of layers of EPTFE including two or more. The layers may be heated for formation of a seal between said layers.

The inside of the tube is coated with a first material and the outside of the tube is coated with a second material. Where the same material is used for the inside and outside of the tube, the coating may be accomplished by immersing the tube in a bath of the coating material or through other suitably coating techniques including spraying the coating, painting the coating onto the tube or extruding the material onto the interior and exterior of the tube. Where different materials are used for the inner and outer layers, the coating may be applied by spraying the tube, painting the material on the tube, extruding the materials or any other suitable application process. Immersion techniques may also be employed if the portion not being coated is appropriately masked.

The resulting tube may either be used directly as a balloon or, more desirably, as a balloon preform for additional processing so as to form a balloon therefrom. In the latter case, the preform may be shaped at a predetermined temperature through suitable balloon forming techniques, as are known in the art. The shaping process may include the application of tension to the balloon so as to stretch it and/or the application of a uniform radial outward force by blowing the preform.

Desirably, the preform will be subject to a temperature ranging from about 70° to about 100° C. and subject to a tension of about 20 g to about 200 g, followed by blowing at pressure of about 200 psi to about 600 psi. Of course, other suitable operational parameters may be used as well. The formation of balloons from preforms is well known in the art and is described for instance in U.S. Pat. No. 4,490,421, in U.S. Pat. No. 5,807,520, and U.S. Pat. No. 5,348,538, all herein incorporated by reference in their entirety.

A balloon with an EPTFE layer may also be prepared by radially expanding a tubular preform containing a PTFE layer.

The invention also contemplates a method of forming an inventive balloon comprising the steps of providing first, second and third tubes, inserting the first tube into the second tube, inserting the second tube into the third tube, inserting the first second and third tubes into a balloon mold and expanding the first, second and third tubes at a desired temperature so as to form a balloon. The second tube is formed of EPTFE.

Another method for forming the inventive balloon comprises the steps of coextruding first, second and third materials so as to form a balloon preform. The second material is a fluoropolymer such as PTFE or a high density polyethylene and is disposed between the first and second materials. Where an EPTFE tube is desired, the balloon preform may be stretched and treated so as to form EPTFE. The resulting balloon preform may be shaped to form a balloon. The shaping may be carried out at a desired temperature and by the placing the preform in tension, by blowing the preform or by a combination of placing the balloon under tension and blowing the balloon or through any other suitable technique known in the art.

The inventive balloons may also be formed by providing a first tube of a first material and disposing a sheet of PTFE, EPTFE, high density polyethylene or other suitable material as disclosed herein around the first tube. A second material may then be disposed around the first tube or the first tube may be placed within a second tube of a second material which serves as the outer skin of the balloon. The materials are then heated to laminate them together or to laminate the material of the first tube to the outer second material. The materials may also be adhesively joined together using suitable adhesives as are known in the art.

It is noted that in the case where an intermediate layer of PTFE is used in a balloon preform, the PTFE may be expanded on blowing the preform so that the PTFE layer in the preform is transformed to an EPTFE layer in the finished balloon.

It is also noted that on blowing the laminated balloon preforms, the intermediate layer such as PTFE, EPTFE, polyethylene or the like may delaminate from the inner and outer layers thereby encapsulating the intermediate layer.

Figure 8:
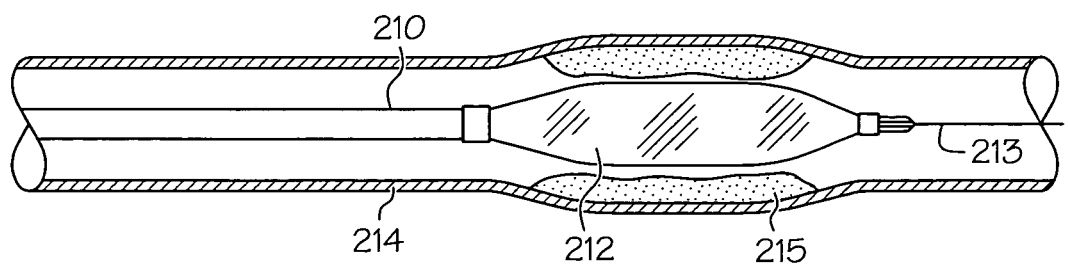
FIG. 8 shows a balloon mounted on a catheter.

In another embodiment, the invention is also directed to a catheter having a medical balloon disposed thereon. FIG. 8 shows a balloon 212 disposed about a catheter tube 210. Guidewire 213 runs through catheter tube 210. Catheter tube 210 is in fluid communication with balloon 212. Alternatively, a separate inflation lumen (not shown) may be provided for inflating the balloon. As further shown in FIG. 8, catheter 210 is in vessel 214 having a lesion 216 therein. Balloon 212 is located in lesion 216 and is shown in a partially inflated state right before dilatation of the vessel.

The inventive balloons disclosed herein are not limited to three layer balloons. More generally, the inventive balloons may be formed of three or more layers of material with at least one intermediate layer of material being of a material selected from the group consisting of fluoropolymers and high density polyethylene as discussed above.

The invention is also directed to other types of catheters including medical device delivery catheters which can employ the inventive balloons. One such suitable stent delivery catheter is disclosed in U.S. Pat. No. 5,772,669 to Vrba. The inventive catheters may be of over-the-wire design, fixed-wire design, rapid exchange design or any other suitable design as is known in the art.

The above disclosure is intended to be illustrative of the present invention, and is not exclusive. This description will suggest many variations and alternatives to one of ordinary skill in this art. All these alternatives and variations are intended to be encompassed within the scope of the attached claims. Those familiar with the art may recognize other equivalents to the specific embodiments described herein which equivalents are also intended to be encompassed by the claims attached hereto.

EXAMPLES

Example 1

The outer and inner layers of a structure balloon was made from tubular preforms which were made of Arnitel® EM-740. A middle layer was formed from ePTFE. The two Arnitel® EM-740 tubes had inside and outside diameters of 0.043 cm (0.017 inches) and 0.079 cm (0.031 inches) respectively for the inner tube and 0.127 cm (0.050 inches) and 0.152 cm (0.060 inches) respectively for the outside tube. The tubes were then assembled together coaxially resulting in a sandwich structure and the assembly was subjected to stretching at room temperature without elongating the ePTFE tube.

The sandwich structure was then inserted into a mold and formed into a 3.0 mm balloon at 95 degrees celcius with a blow pressure of 450 psi (31 atm) and tension of 70 grams. The resultant three-layer balloon had a wall thickness of 0.00643 cm (0.00253 inches), a compliance of 5.1% at 6-12 atm and 5.5% at 12-18 atm and burst pressure was 353 psi (24 atm).

The resultant balloon had a much higher puncture resistance than a single layer balloon made from Arnitel® EM-740 only with the same wall thickness.

The resultant balloon had a sandwich structure.

What is claimed is:

1. A method of forming a balloon comprising at least three layers comprising the steps of:
   i) providing first, second and third tubes, the second tube formed of a tube made of a material selected from the group consisting of fluoropolymers and high density polyethylene;
   ii) inserting the first tube into the second tube;
   iii) inserting the second tube into the third tube;
   iv) inserting the first, second and third tubes into a balloon mold;
   v) expanding the first, second and third tubes at a desired temperature so as to form a balloon.

2. A method of forming a balloon comprising at least three layers comprising the steps of:
   i) providing first, second and third tubes, the second tube formed of expanded PTFL;
   ii) inserting the first tube into the second tube;
   iii) inserting the second tube into the third tube;
   iv) laminating the first tube and the second tube together;
   v) laminating the second tube and third tube together so as to form at least a three tube laminate.

3. The method of claim 2 further comprising the step of laminating the first and third tubes together at least in part.

4. The method of claim 2 further comprising the step of blowing the laminate at a predetermined temperature.

5. The method of claim 4 wherein the first and second tubes and the second and third tubes delaminate upon blowing the balloon.

* * * * *

UNITED STATES PATENT AND TRADEMARK OFFICE
CERTIFICATE OF CORRECTION

| | | |
|---|---|---|
| PATENT NO. | : 7,682,553 B2 | Page 1 of 1 |
| APPLICATION NO. | : 10/797996 | |
| DATED | : March 23, 2010 | |
| INVENTOR(S) | : Wang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C 154(b) by 1708 days.

Signed and Sealed this
Eighteenth Day of January, 2011

David J. Kappos
*Director of the United States Patent and Trademark Office*